United States Patent [19]

Lucietto et al.

[11] Patent Number: 5,856,305
[45] Date of Patent: Jan. 5, 1999

[54] PEPTIDES ENDOWED WITH ANTIINFLAMMATORY ACTIVITY

[75] Inventors: Pierluigi Lucietto; Paola Giuliani; Gianluca Fossati; Paolo Mascagni; Gianni Gromo, all of Sesto S. Giovanni, Italy

[73] Assignee: Italfarmaco S.P.A., Milan, Italy

[21] Appl. No.: 836,195

[22] PCT Filed: Nov. 20, 1995

[86] PCT No.: PCT/EP95/04566

§ 371 Date: Jul. 17, 1997

§ 102(e) Date: Jul. 17, 1997

[87] PCT Pub. No.: WO96/16083

PCT Pub. Date: May 30, 1996

[30] Foreign Application Priority Data

Nov. 21, 1994 [IT] Italy .................................. MI94A2358

[51] Int. Cl.$^6$ ............................ A61K 38/16; C07K 14/35
[52] U.S. Cl. .............................................. 514/12; 530/324
[58] Field of Search ................................. 514/12; 530/324

[56] References Cited

PUBLICATIONS

Tisch R and McDevitt, HO. Proc. Natl. Acad. Sci. USA 91:437–438, Jan. 1994.

Wraith DC, et al., Cell, 59:247–255, 1989.

Winfield JB, Arthritis and Rheumatism, 32:1497–1503, Dec. 1989.

Thomas, CL. Tabor's Cylopedic Medical Dictionary. FA Davis Co., Philadelphia, PA., 1981.

*Primary Examiner*—Christina Y. Chan
*Assistant Examiner*—Mary Beth Tung
*Attorney, Agent, or Firm*—Walter H. Schneider

[57] ABSTRACT

Peptides endowed with antiinflammatory activity consisting of 25 aminoacids having a sequence with an homology of at least 25% with the 1-25 fragment of the 10 Kda heat shock protein from Mycobacterium tuberculosis.

**3 Cla

PEPTIDES ENDOWED WITH ANTIINFLAMMATORY ACTIVITY

This application is a 371 of PCT/EP95/04566 filed Nov. 20, 1995.

BACKGROUND OF THE INVENTION

1. Field of the Invention

The present invention relates to peptide derivatives of heat shock proteins, and to the use thereof in the treatment of inflammatory pathologies.

2. Description of the Related Art

The heat shock proteins (hereinfrom "HSP") are produced by cells under stress conditions, especially by mycobacteria. Procaryotes such as mycobacteria, express high HSP levels, some of which, e.g. a 65 kD protein, are immuno-dominant antigens, thus their use as vaccine was envisaged, e.g. antitubercolotic vaccine [(Kaufmann, S. H. E. et al., Eur. J. Immunol., 17, 351 (l987)]. WO 89/12455 gives a hint about the use of a protein of such class or a fragment thereof, specifically referring to a 65 kD protein, as a vaccine against non-viral infections and to induce an immune response.

Specific proteins within the same class were described as useful in different pathologies. For example, WO 90/10449 relates to the use of a HSP of 65 kD as a diagnostic agent and in the treatment of the insulin-independent diabetes. The same protein was found to posses a mycobacterial-specific epitope envolved in the pathogenesis of the auto-immune arthritis [Gaston, J. F. et al., Nature, 331, 171 (1988)].

The HSP sequence weighing 10 kD is disclosed by Baird, P. N. et al., J. Gen. Microb., 135, 931–939 (1989) which describes it as coming from *Mycobacterium tuberculosis* BGC, while Mehra, V. et al., J. Exp. Med., 175, 275–284 (1992) discloses a homologous protein having the same weight from *Mycobacterium leprae*. Barnes, P. F. et al., J. Immun., 148, 1835–1840 (1992) discloses a 10 kD protein coming from *Mycobacterium tuberculosis* as highly immuno-reactive antigen hypothetically useful as anti-tuberculotic vaccine. Hartman, D. J. et al., Proc. Natl. Acad. Sci. USA, 89, 3394–3398 (1992) identified, in the mammal, a protein homologous to the 10 kD proteins described in the literature above mentioned.

SUMMARY OF THE INVENTION

It has been now found that peptides of 25 amino acids having a sequence corresponding to or with a homology of at least 25% with the 1–25 fragment of the HSP from *Mycobacterium tubercolosis*, are endowed with antiinflammatory activity.

Therefore, the invention relates to a peptide of 25 amino acids having a homology $\geq 25\%$ with the following amino acid sequence I (Sequence Id No. 1):
$NH_2$-Ala Lys Val Asn Ile Lys Pro Leu Glu Asp Lys Ile Leu Val Gln Ala Asn Glu Ala Glu Thr Thr Thr Ala Ser-OH
wherein the N-terminus is optionally acylated.

A preferred emboidment is a 1–25 peptide having the amino acid sequence I.

Said peptides are useful in the treatment of inflammatory pathologies, especially in the treatment of rheumatoid arthritis.

The peptides of the invention are prepares by conventional chemical methods of peptide synthesis. A method is the one in solid phase originally developed by Merrifield, R. B. (Biochemistry 1964, 3, page 1385; The Peptide 1979, 2, page 1–284, E. Gross and J. Meienhofer Ed.). Alternatively, the synthesis may be carried out, always in solid phase, applying the flow method and using Fmoc-amino acids optionally protected on the side-chain by acid-labile groups [Atherton E. and Sheppard R. C., "Solid phase peptide synthesis—a practical approach", IRL PRESS, Oxford, 1989]. In the latter case a commercially available automatic or semiautomatic synthetizer (e.g., MILLIGEN® 9050) is used, and the solid support may be one of the resins suitable to this synthetic method (e.g., NOVASYN® resins of Novabiochem, or PEPSYN® resins of Milligen KA). Usually, these resins contain norleucine residues (as internal reference amino acid) to which the reversible anchoring agent for the peptide to be prepared may then be linked. The anchorage agent may be, for example, p-hydroxymethyl-phenoxyacetic acid. In this case, among the commercially available resins, the ones just containing the protected derivative of the first amino acid linked by an ester bond to the resin may be employed.

Generally, in any case the peptide synthesis is carried out through a series of deprotection cycles with 20% piridine in dimethylformamide (DMF), repeated short washings with DMF, acylation and again repeated washings with DMF, according to the standard procedures provided by the synthetizer manufacturer and the modifications thereof obvious to the skilled in the art, which are automatically performed by the apparatus. The single protected amino acids are used as activated esters to assemble the peptide, such ester being pre-formed and commercially available, or prepared in situ without isolation, for example as phenolic esters or as 1-hydroxy-benzotriazol or 3-hydroxy-4-oxo-3,4-dihydro-1, 2,3-benzotriazine esters or analogues thereof. Actually, the suitably protected amino acid is reacted with a condensing agent such as, for example, di-cycloalkyl-carbodiimide, di alkyl-carbodiimide or benzo-triazol-1-yl-oxy-tris-(dimethylamino)-phosphonium hexa-fluorophosphate (BOP) and analogues thereof, in the presence of the selected phenolic derivative such as, e.g. pentafluorophenol or of 1-hydroxy-benzotriazole (HOBT) or 3-hydroxy-4-oxo-3,4-dihydro-1,2,3-benzotriazine (HODhbt). For each condensation a 4 times excess with respect to the amino groups was used. At the end of the synthesis, the peptide may be removed from the resin by means of one of the protocols known to the skilled in the art. For example, 0.5 g of resin+peptide suspended in about 10 ml of a mixture of 90% trifluoroacetic acid (TFA), 5% thioanisole, 3% ethandithiole, 2% anisole, is kept at room temperature, under mild stirring and under nitrogen for 4 hours. The mixture is then directly filtered in a 10–20 times bigger volume of ethyl ether cooled in ice-bath. The precipitate is filtered or centrifuged, then dried under vacuum overnight. The peptide is dissolved in a suitable buffer and freeze-dried. Another method employs the suspension of 0.5 g of resin+peptide in about 25 ml of a mixture of 1M trimethyl-silyl-bromide (Me3SiBr) 1M thioanisole, 0.25M ethandiole in trifluoroacetic acid, and maintaining the whole at 0° C. under mild stirring and under nitrogen for 1 hour. The resin is then filtered and washed with a small volume of pure TFA. The solvent is evaporated, and the residue tritured in ethyl ether is filtered or centrifuged, then dried under vacuum overnight. The peptide is dissolved in a suitable buffer and freeze-dried.

DESCRIPTION OF THE PREFERRED EMBODIMENT

The following example better illustrates the invention.

EXAMPLE

Sinthesis of the 1–25 fragment of HSP-10 from
*Mycobacterium tuberculosis*

Sequence: H-Ala Lys Val Asn Ile Lys Pro Leu Glu Asp Lys Ile Leu Val Gln Ala Asn Glu Ala Glu Thr Thr Thr Ala Ser-OH The solid support [1 g of Fmoc-Ser(tBu)-PEPSYN® KA (100); resin substitution 0.09 mmol/g] was charged on the column of a MILLIGEN® 9050 synthetizer and submitted to a standard series of deprotection and acylation cycles. Each single amino acid residue employed had the α-amino group protected with Fmoc, whereas the protecting group of the side-chains were tert-butyloxycarbonyl (Boc) for lysine, tert-butyl (tBu) for aspartic and glutamic acid, serine and threonine. All of the so protected amino acids were pre-activated as pentafluorophenol ester excepting for serine and threonine, pre-activated as HODhbt esters. Each single residue was sequentially assembled (in a 4 times molar excess) starting from the C-terminus amino acid, through single and/or double coupling cycle in about 60 minutes. The final cleavage of the peptide from the resin and the detachment of the protecting groups from the side-chains were effected on a scale of 0.5 g of peptide-resin following one of the protocols above described. After freeze-drying, there were obtained 100 mg of crude peptide (molecular weight=2684; calculated yield: 120 mg), yield 83%. 50 mg were charged on a semi-preparative reversed-phase column (Vydac C4, 25×1 cm), balanced with eluent A) 0.085% TFA in water, and eluted with eluent B) 0.085 TFA in acetonitrile:water 80:20, applying a gradient of 0.27% B/minute at a flow of 3.0 ml/minute. There were thus obtained 13 mg of a product with a final yield over the crude of 26%. The relative purity of the peptide was determined by HPLC analysis on a reversed-phase Vydac C4 column (150×4.6 mm), using as eluent A) 0.045% TFA in water:acetonitrile (98:2 v/v) and as eluent B) 0.036% TFA in acetonitrile, with a gradient of 2% B/minute.

The amino acid composition of the peptide (Tab. 1) was determined by an amino acid BECKMAN System Gold 126 AA analyzer, after hydrolysis at 110° C. for 22 hours in 6N HCl in the presence of 1% phenol v/v, in sealed vials under vacuum: peptide content 88%. The molecolar weight of the peptide was determined by mass spectrometry (BIOMASS spectrometer, ELECTRO-SPRAY ionizer, quadrupole, accuracy 0.05–0.01%): calculated 2684; found 2684.

TABLE 1

| Amino acid | calculated | found |
| --- | --- | --- |
| Asp/Asn | 3 | 3.01 |
| Thr | 3 | 2.92 |
| Ser | 1 | 0.63 |
| Glu/Gln | 4 | 3.85 |
| Pro | 1 | 1.03 |
| Ala | 4 | 3.99 |
| Val | 2 | 1.96 |
| Ile | 2 | 1.87 |
| Leu | 2 | 2.03 |
| Lys | 3 | 3.09 |

The peptide of the present invention is useful in the treatment of inflammatory pathologies of different kinds and origins, as it is shown by pharmacological test (adjuvant arthritis test) as follows.

15 Wistar rats (C. River; weight 130–140 g) and anaesthetized with $CO_2$, were intradermically administered (injection at the base of the tie) with 0.1 ml of a suspension of 10 mg/ml of heat-inactivated *M. tuberculosis* (Strain C, DT and PN; Central Vet. Labs—GB), in sterile paraffin oil. The rats were divided in 3 groups of 5 animals each, and at day 4, 5 and 6 from the above treatment, following the same method for inducing arthritis, they were administered with 50 μg/rat dose of the peptide I in 100 μl of PBS for the first group, with PBS only for the second group, while the third group was not treated. The course of the arthritis was monitored according to the following scheme of clinical scores:

| score | symptomatology |
| --- | --- |
| 0 | no inflammation |
| 1 | slight redness and swelling of the paws |
| 2 | swelling of the paws such that the tendons are no longer visible |
| 3 | swelling extending to the ankle joint |
| 4 | marked inflammation and deformity of the ankle joint |

The scores range from 0 to 4 for each paw; furthermore one additional score is assigned if there are nodules on the tie, and another futher score is assigned if ears are involved, thereby the score is 0 at minimum and 18 at maximum.

The results are set forth in Tables 2 and 3.

TABLE 2

| | Clinical scores (± S.E.) | | | | | |
| --- | --- | --- | --- | --- | --- | --- |
| Treatment | day 7 | day 8 | day 10 | day 11 | day 12 | day 13 |
| 1–25 | 0 | 0 | 0.6 ± 0.6 | 3.8 ± 0.4 | 10.0 ± 0.7 | 12.6 ± 0.6 |
| PBS | 1.4 ± 0.2 | 1.8 ± 0.4 | 7.4 ± 1.3 | 11.6 ± 0.6 | 14.8 ± 0.4 | 15.6 ± 0.6 |
| Control | 0.2 ± 0.2 | 1.4 ± 0.4 | 5.8 ± 1.1 | 9.4 ± 0.7 | 13.4 ± 1.2 | 15.4 ± 0.6 |

TABLE 3

| | Incidence of arthritis (arthritic rats/total rats) | | | | |
| --- | --- | --- | --- | --- | --- |
| Treatment | day 7 | day 8 | day 10 | day 11 | day 12 |
| 1–25 | 0/0 | 0/0 | 1/5 | 5/5 | 5/5 |
| PBS | 5/5 | 5/5 | 5/5 | 5/5 | 5/5 |
| Control | 1/5 | 4/5 | 5/5 | 5/5 | 5/5 |

An object of the present invention is therefore the use above mentioned peptides in the treatment of inflammatory pathologies, referring to all the industrial aspects connected to said use also including their incorporation into pharmaceutical compositions. For the envisaged pharmaceutical uses, the peptides of the invention may be administered suitably formulated into pharmaceutical compositions for parenteral administration, particularly intradermically, subcutaneously and intra-articularly injectable formulations. As for the intradermically and subcutaneously injectable formulations, the active principal may be dissolved in bidistilled water, optionally in the presence of isotonic agents such as dextrose or sodium chloride, antimicrobials such as p-hydroxy-benzoates, and buffers, for example a phosphate buffer such as PBS. As for the intra-articularly injectable formulations, it is necessary for the presence of an isotonic agent such as one of the already above said, together with the other just mentioned excipients. The active principal may also be formulated as a restorable freeze-dried product containing from 4 to 8% of mannitol or lactose. Obviously the posology depends from various parameters such as the kind and severity of the pathologies to be treated, and the conditions of the patient (weight, sex, age, etc.).

We claim:

1. A peptide having the sequence of SEQ ID NO:1 as follows:

NH$_2$-Ala Lys Val Asn Ile Lys Pro Leu Glu Asp Lys Ile Leu Val Gln Ala Asn Glu Ala Glu Thr Thr Thr Ala Ser-OH optionally acylated at the N-terminus.

2. A pharmaceutical composition having rheumatoid arthritic anti-inflammatory properties containing as the principal active ingredient an effective amount of a peptide according to claim 1 together with a pharmaceutically acceptable carrier.

3. A method of treating a patient suffering from inflammatory rheumatoid arthritis which comprises administering to said patient an effective amount of a composition according to claim 2.

* * * * *

SEQUENCE LISTING ( 1 ) GENERAL INFORMATION:

( i i i ) NUMBER OF SEQUENCES: 1

( 2 ) INFORMATION FOR SEQ ID NO: 1:

( i ) SEQUENCE CHARACTERISTICS:
      ( A ) LENGTH: 25 amino acids
      ( B ) TYPE: amino acid
      ( D ) TOPOLOGY: linear ( i i ) MOLECULE TYPE: peptide ( v ) FRAGMENT TYPE: N-terminal ( v i ) ORIGINAL SOURCE:
      ( A ) ORGANISM: Mycobacterium tuberculosis ( x i ) SEQUENCE DESCRIPTION: SEQ ID NO: 1:

```
Ala  Lys  Val  Asn  Ile  Lys  Pro  Leu  Glu  Asp  Lys  Ile  Leu  Val  Gln  Ala
 1              5                        10                       15
Asn  Glu  Ala  Glu  Thr  Thr  Thr  Ala  Ser
           20                       25
```